United States Patent [19]

Warren et al.

[11] 4,221,800
[45] Sep. 9, 1980

[54] CYCLOALKENOCHROMONE

[75] Inventors: Brian T. Warren, Ickenham; John W. Spicer, High Wycombe; Thomas Miller, Harefield, all of England

[73] Assignee: Miles Laboratories, Inc., Elkhart, Ind.

[21] Appl. No.: 863,688

[22] Filed: Dec. 23, 1977

[51] Int. Cl.² .............. C07D 257/04; C07D 311/78; A61K 31/35; A61K 31/41
[52] U.S. Cl. .................... 424/269; 424/275; 424/283; 260/345.2; 548/253; 549/45; 549/46; 549/27
[58] Field of Search ............ 260/308 D, 345.2, 327 R, 260/328, 327 B; 424/269, 283, 275; 548/253; 549/45, 46, 27

[56] References Cited

U.S. PATENT DOCUMENTS

| | | | |
|---|---|---|---|
| 3,232,945 | 2/1966 | Sigal et al. | 546/103 |
| 3,244,720 | 4/1966 | Meschino | 546/103 |
| 3,755,319 | 8/1973 | Bays | 260/308 D |
| 3,886,162 | 5/1975 | Pfister et al. | 546/103 |
| 3,905,989 | 9/1975 | Hodson et al. | 260/328 |
| 3,947,449 | 3/1976 | Durchheimer et al. | 546/103 |

Primary Examiner—Glennon H. Hollrah
Assistant Examiner—D. B. Springer
Attorney, Agent, or Firm—James D. McNeil

[57] ABSTRACT

Certain substituted cycloalkenochromones and pharmacologically acceptable salts thereof are disclosed as being useful in the treatment of allergies. The compounds have the structure:

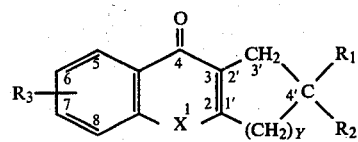

X is —O—, —S—, or —SO₂. Y is from 1 to 4. $R_1$ is H or alkyl, and $R_2$ is H, alkyl, aryl, carboxyl, alkoxy, aralkoxy, or alkoxycarbonyl. When $R_1$ is alkyl, $R_2$ is hydrogen, alkyl or aryl. At least one of $R_2$ and $R_3$ is alkoxycarbonyl, carboxyl or tetrazolyl. $R_3$ is carboxyl, alkylthio, alkylsulfonyl, alkylsulfinyl, alkoxycarbonyl, or tetrazolyl.

36 Claims, No Drawings

CYCLOALKENOCHROMONE

BACKGROUND OF THE INVENTION

1. Field of the Invention

Hypersensitive individuals undergo an altered state as a result of contact with the antigens from an allergen leading to the formation of antibodies thereto. Subsequent contact with one of those antigens or a structurally similar substance can evoke in an allergic individual a pathological reaction, due to the presence of antibodies. When these individuals inhale or ingest the offending antigen, a prominent manifestation includes bronchial asthma.

Allergic responses are involved with the production within an individual of a type of tissue-sensitizing IgE antibody called a reagin. These IgE antibodies have a high affinity for receptors on cells present in various body tissues. The receptors are on mast cells which are found in close association with capillaries in connective tissues throughout the body and on basophilic leukocytes (blood cells). Mast cells and basophils contain a high content of pharmacologically-active mediators or spasmogens, such as histamine, serotonin (5-hydroxytryptamine) and kinins (basic peptides), concentrated in cytoplasmic granules. Contact of the IgE antibodies, which are fixed to mast cells and basophils, with antigens can trigger cross-linking of the IgE antibodies. In turn, this cross-linking causes degranulation of mast cells and basophils, which releases the chemical mediators and produces manifestations of the allergic response, eg., bronchial asthma referred to earlier. In order to reduce the undesirable allergic responses, it has been suggested in the prior art to administer various compounds which have an antiallergic characteristic of interfering with the degranulation of mast cells and basophils. There is a need for such antiallergic compounds having increased efficacy over known compounds.

2. Description of the Prior Art

Japanese Patent Publication No. 52.039677 (KOWA) describes xanthene derivatives which are useful as antiallergic agents or in drugs for treating asthma. The compounds disclosed have the formula:

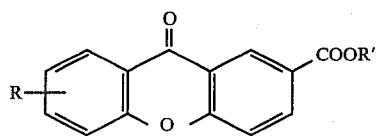

in which R is hydrogen, lower alkyl, hydroxy, lower alkoxy, hydroalkoxy, halogen or trifluoromethyl. R' is hydrogen or lower alkyl.

KOWA discloses that the xanthene compounds are produced by dehydrogenation of the corresponding tetrahydroxanthene compounds. These intermediate tetrahydroxanthene compounds have the structure:

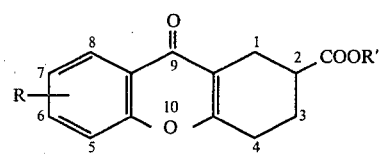

wherein R and R' are defined as above. The intermediates are disclosed by KOWA as having "antiinflammatory, antiallergic and blood sugar lowering activities." All of the tetrahydroxanthenes disclosed by KOWA have a COOR' substitutent at the 2-position and, if substituted at the 6, 7 or 8-position, have an —OH; —OCH$_3$; —O—C$_2$H$_4$—OH; —Cl, —CH$_3$ or —CF$_3$ present. There is no disclosure or suggestion that the 2-position can be substituted with an alkyl chain or disubstituted; that the oxygen atom in the 10-position can be replaced by —S, or —SO$_2$; or that R can be carboxyl, alkylthio, alkylsulfonyl, alkylsulfinyl, alkoxycarbonyl or tetrazolyl.

SUMMARY OF THE INVENTION

The present invention is directed to cycloalkenochromones having anti-allergic properties. The cycloalkenochromones and pharmacologically acceptable, non-toxic salts thereof, are represented by the formula:

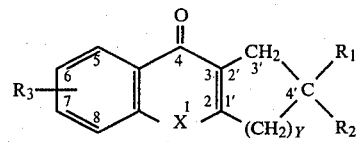

X is —O—, —S—, or —SO$_2$. Y is 1 to 4. R$_1$ is hydrogen or alkyl, and R$_2$ is H, alkyl, aryl, carboxyl, alkoxy, aralkoxy, carboxyl or alkoxycarbonyl. When R$_1$ is alkyl, R$_2$ is hydrogen, alkyl or aryl. R$_3$ is carboxyl, alkythio, alkylsulfonyl, alkylsulfinyl, alkoxycarbonyl or tetrazolyl, with the proviso that at least one of R$_2$ and R$_3$ is carboxyl, alkoxycarbonyl or tetrazolyl.

DETAILED DESCRIPTION OF THE INVENTION

Compounds of Formula I wherein R$_3$ is alkylthio, alkylsulfinyl, alkylsulfonyl or alkoxycarbonyl, and X is —O— or —S— can be produced by the reaction of a mixed anhydride of a substituted acetylsalicylic acid and an enamine, as illustrated below. Y, R$_1$ and R$_2$ are as defined hereinbefore.

$$\overset{N}{|}$$

preferably represents pyrrolidino, piperidino or morpholino, and Z is a radical of formula OCOOR$_4$ in which R$_4$ is an alkyl of 1 to 4 carbon atoms, preferably ethyl.

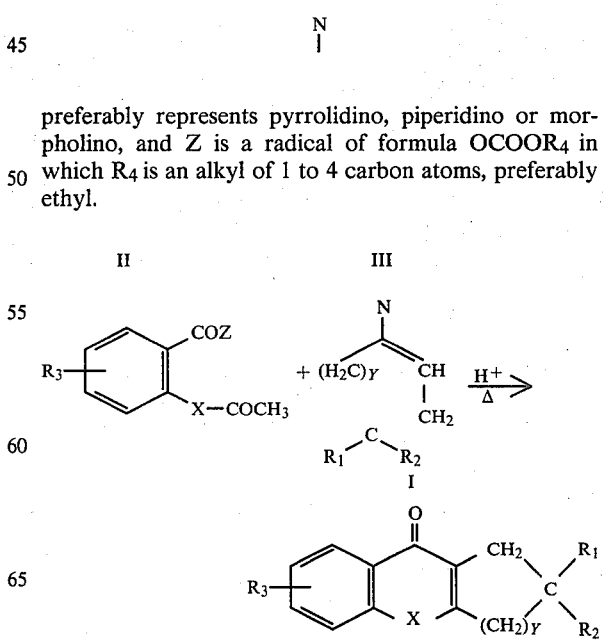

Substituted salicylic acids are commercially available and may be acetylated by a procedure such as that described by Drain et al., *J. Chem. Soc.* 1498 (1949). The preparation of 5-iodothiosalicylic acid and its acetyl derivative is described in Example 33. Preparation of the 4-iodothiosalicylic acid starting material is described in Example 37; the 4-iodothiosalicylic acid is used to prepare 7-substituted cycloalkenothiochromones.

Starting materials for preparation of cycloalkenothiochromones wherein X is —$SO_2$— are derived from compounds described herein where X is S. Where $R_3$ is alkylsulfonyl or alkysulfinyl, commercially available alkylthiosalicylic acid has been utilized to synthesize the alkylthio-substituted cycloalkenochromone; the latter is then oxidized to the corresponding alkylsulfonyl or alkylsulfinyl compound.

Enamines may be readily prepared by procedures described by J. Szmuszkovicz in *Enamines, Advances in Organic Chemistry—Method and Results*, Vol. 4, Interscience Publishers (1963).

The general procedure used is that described by Boyd, et al., *J. Chem. Soc.* 935 (1969). The compounds of Formula II and III react together to form an intermediate which is not isolated but which is cyclized immediately by heating with acid, e.g. hydrochloric, to produce a compound of Formula I.

It has been found that the yield of certain cycloalkenochromones, e.g., the compound described in Example 30 was undesirably low when the procedure of Boyd was used. When the Boyd procedure is modified to substitute a 1-imidazolyl radical for Z, it has been found that a greatly increased yield is obtained and that further treatment of the acylation product, either by heating with hydrochloric acid or a mixture of pyridine, water and piperidine, is eliminated.

Introduction of the 1-imidazolyl radical referred to above, is easily effected by adding 1,1'-carbonyldiimidazole to the appropriate acetylsalicylic acid in a dry solvent and stirring the mixture until evolution of $CO_2$ ceases. On addition of the enamine of Formula III to the imidazolide solution obtained, the chromone of Formula I (where $R_3$ is CN) is spontaneously produced at room temperature without any addition of catalyst being required.

The mixed anhydride of Formula II can be prepared by methods well known in the art. For example, the mixed anhydride can be prepared from a suitable salt of the acid, preferably the triethylamine salt, by reaction with a chloroformate ester, preferably ethyl chloroformate.

Compounds of Formula I in which $R_3$ is carboxyl or tetrazolyl can be made by reaction of a corresponding halogeno compound, designated as Formula IV, preferably iodo, with a metallic cyanide, preferably cuprous cyanide, in a suitable solvent such as dimethylformamide (DMF) or N-methyl pyrrolidone, at elevated temperature. The cyano intermediate, designated as Formula V, is hydrolyzed under acid conditions to produce a compound of Formula I in which $R_3$ is carboxyl. The hydrolysis may be preferably carried out with a mixture of acetic acid and 50 percent v/v sulfuric acid under reflux conditions. When $R_3$ is tetrazolyl, the cyanide intermediate is reacted with sodium azide to produce a compound of Formula I. The reaction with sodium azide is preferably carried out in the presence of ammonium chloride in DMF at an elevated temperature, for example 90° to 100°. Alternatively, the compounds of Formula V may be made from the corresponding amino compounds of Formula IVa by diazotization.

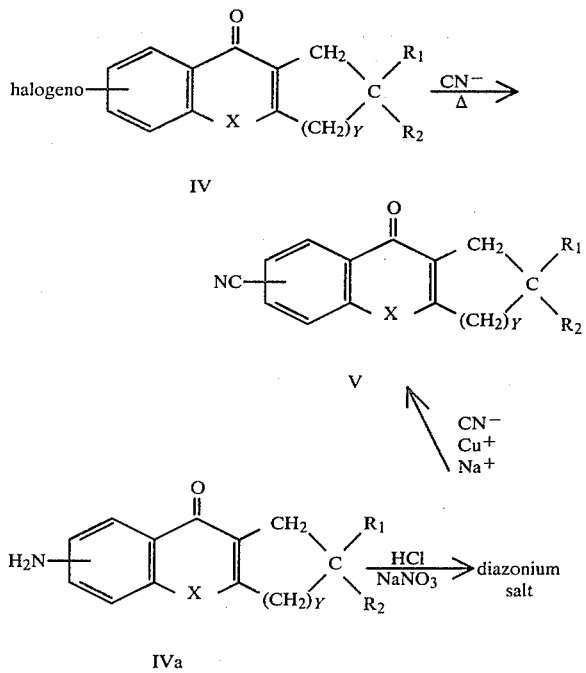

For example, amino compound can be reacted with a mixture of hydrochloric acid and sodium nitrite to form a diazonium salt which is treated with a mixture of cuprous and sodium cyanides to produce the cyano intermediate V.

The amino compounds of Formula IVa, from which the cyano compounds of Formula V can be prepared in the manner indicated above, can themselves be obtained by reduction of the corresponding nitro compounds, or by hydrolysis of the corresponding acylamino compounds. Suitable procedures are well known in the art.

The halogeno compounds of Formula IV from which the cyano compound of Formula V can be made as described above, and the nitro and acylamino compounds just mentioned, can all be prepared by condensation of a corresponding acetylsalicylic acid or acetylthiosalicylic acid derivative with an enamine of Formula III in the manner already indicated. Suitable methods of carrying out these reductions are illustrated in the Examples below.

As described before, the compounds of Formula I in which X is —$SO_2$— and/or $R_3$ is alkylsulfonyl can be made from corresponding compounds in which, in Formula I, X is —S— and/or $R_3$ is alkylthio, by oxidation. Suitable oxidizing agents for the oxidation of sulfur atoms to sulfonyl groups can be used for this purpose. For example, oxidation with hydrogen peroxide in acetic or formic acid is suitable. Suitable oxidizing agents for the oxidation of sulfur atoms to sulfinyl groups includes sodium metaperiodate. The compounds of Formula I wherein X is —$SO_2$— can be prepared by oxidation of corresponding compounds in which X is —S—.

Preferred compounds are those in which Y is 2, $R_1$ is hydrogen, $R_2$ is ethyl, and $R_3$ is tetrazolyl, or $R_2$ is carboxyl and $R_3$ is methylthio, methylsulfonyl, or methylsulfinyl. The radical $R_3$ is preferably in the 6- or 7-position.

The following examples illustrate the production of the compounds of the present invention. Temperatures are in ° C.

EXAMPLE 1

6-Carboxy-2,3-cyclohexenochromone (a) 6-Iodo-2,3-cyclohexenochromone

Triethylamine (10.1 g) was added to a stirred suspension of 5-iodoacetylsalicylic acid (30.6 g) in dry chloroform (100 ml) below 5°. The resulting solution was cooled below −10° by means of a cooling bath. Ethyl chloroformate (10.9 g) was added at a rate to prevent the temperature from rising above −5°. After 10 minutes, 1-(N-piperidino) cyclohexane (16.1 g) was added dropwise to the cooled solution. After completion of the addition, the cooling bath was removed and the reaction mixture was stirred for 20 hours at room temperature. Concentrated hydrochloric acid (70 ml) was then added and the mixture heated under reflux for 4 hours with stirring. After cooling, the organic layer was separated and the aqueous phase was extracted with chloroform (50 ml). The organic phase and extracts were washed successively with water, sodium carbonate solution and water, and then dried over magnesium sulphate. Following removal of the solvent 6-iodo-2,3,-cyclohexenochromone (15.55 g), m.p. 150°–151.5° was obtained.

Calcd for $C_{13}H_{11}IO_2$: C, 47.87; H, 3.40; I, 38.92%. Found: C, 47.61; H, 3.44; I, 39.17%.

(b) 6-Cyano-2,3-cyclohexenochromone

A mixture of 6-iodo-2,3-cyclohexenochromone (4.55 g) and cuprous cyanide (1.4 g) in dimethylformamide (15 ml) was heated under reflux for two days. The pale yellow crystals (1.75 g) m.p. 205°–206° which separated after cooling were collected. The filtrate was poured into a solution of ferric chloride hexahydrate (3.0 g) in concentrated sulphuric acid (9 ml) and water (9 ml), and warmed on a water-bath for 30 minutes. After cooling, the solution was extracted with ether, washed with 10 percent sodium bisulphite solution and dried (magnesium sulphate). Concentration of the solution yielded a further 0.5 g of 6-cyano-2,3-cyclohexenochromone, m.p. 203°–206°.

Calcd for $C_{14}H_{11}NO_2$: C, 74.65; H, 4.92; N, 6.22%. Found: C, 74.69; H, 4.70; N, 6.21%.

The cyano intermediate was converted into the desired cycloalkenochromone as described below.

(c) Fifty percent sulphuric acid (6 ml) was added to 6-cyano-2,3-cyclohexenochromone (1 g) in glacial acetic acid (3 ml) and the mixture was heated under reflux for four hours. After cooling, the reaction mixture was added dropwise with stirring to distilled water (100 ml) and the creamy-white solid that separated was collected. The product was dissolved in saturated sodium hydrogen carbonate solution (80 ml), treated with charcoal, filtered and then reprecipitated by the addition of dilute hydrochloric acid. On drying, the desired 6-carboxy-2,3-cyclohexenochromone (1.1 g), m.p. 262°–263°, was obtained.

Calcd for $C_{14}H_{12}O_4$: C, 68.84; H, 4.95%. Found: C, 68.18; H, 4.64%.

The procedure was repeated to obtain additional cycloalkenochromone compound.

The sodium salt was prepared as follows. A solution of sodium hydrogen carbonate (0.84 g) in water (25 ml) was added to 6-carboxy-2,3-cyclohexenochromone (2.44 g) and warmed until the solid dissolved. The hot solution was treated with charcoal, filtered, and the resulting solution was freeze-dried to yield sodium 2,3-cyclohexenochromone-6-carboxylate (2.52 g) m.p. 322°–324°, decomposition.

Calcd for $C_{14}H_{11}O_4Na.2H_2O$: C, 55.62; H, 5.00%. Found: C, 55.51; H, 5.14%.

EXAMPLE 2

6-(5-(1H)-tetrazolyl)-2,3-cyclohexenochromone (a) Sodium azide (0.18 g) and ammonium chloride (0.15 g) were added to a solution of 6-cyano-2,3-cyclohexenochromone (0.56 g) in dimethylformamide (5 ml) and the mixture was heated at 100° for three hours. After cooling, the mixture was added dropwise with stirring to water (100 ml), cooled to 4° for one hour and filtered. The filtrate was acidified to pH 1 and the resultant precipitate collected by filtration and dried to yield 6-(5-(1H)-tetrazolyl)-2,3-cyclohexenochromone (0.34 g), m.p. 301°–303°.

Calcd for $C_{14}H_{12}N_4O_2$: C, 62.68; H, 4.51; N, 20.89%. Found: C, 62.54; H, 4.66; N, 21.11%.

The sodium salt was prepared as described below.

(b) A solution of sodium hydrogen carbonate (0.168 g) in water (25 ml) was added to 6-(5-(1H)-tetrazolyl)-2,3-cyclohexenochromone (0.53 g) and warmed on a water bath for two hours. The solution was filtered, cooled and freeze-dried to yield sodium 6-(5-(1H)-tetrazolyl-2,3-cyclohexenochromone (0.6 g), m.p. greater than 340°.

Calcd for $C_{14}H_{11}N_4O_2Na.3\frac{1}{2} H_2O$: C, 47.57; H, 5.13; N, 15.86%. Found: C, 47.77; H, 4.98; N, 15.79%.

EXAMPLE 3

6-Carboxy-2,3-(4′-methylcyclohexano)chromone (a) 6-Iodo-2,3-(4′-methylcyclohexeno)chromone Triethylamine (10.1 g) was added to a stirred suspension of 5-iodoacetylsalicylic acid (30.6 g) in dry chloroform (100 ml) below 5°. The resulting solution was cooled to −20° and ethyl chloroformate (10.9 g) was added. The temperature increased to −7° during the addition. Fifteen minutes later, 1-(N-piperidino)-4-methylcyclohexene (17.0 g) was added dropwise between −5° and 0°. The reaction mixture was allowed to attain room temperature and stirring was continued for 4½ hours. Concentrated hydrochloric acid (70 ml) was added and the mixture was refluxed for 4½ hours. After cooling, the aqueous phase was separated, extracted with chloroform (50 ml) and the combined chloroform layers were washed successively with water, sodium carbonate solution and water. Removal of the solvent gave an oil which on trituration with ice-cold ether yielded 6-iodo-2,3-(4′-methylcyclohexeno)-chromone (13.9 g), m.p. 173°–178°.

Calcd for $C_{14}H_{13}IO_2$: C, 49.41; H, 3.85; I, 37.30%. Found: C, 48.75; H, 4.08; I, 37.52%.

(b) 6-Cyano-2,3-(4′-methylcyclohexeno)chromone

A solution of 6-iodo-2,3-(4′-methylcyclohexeno)-chromone (14.24 g) and cuprous cyanide (4.19 g) in dimethylformamide (45 ml) was heated under reflux (48 hours). The hot reaction mixture was filtered, cooled and pale yellow crystals were collected. The filtrate was heated on a steam bath for 30 minutes with a solution containing ferric chloride hexahydrate (7.5 g) concentrated sulphuric acid (23 ml) and water (23 ml). After cooling, the mixture was extracted with ether (1×150, 2×100 ml) and the combined extracts were washed with 10 percent sodium bisulphite solution (2×25 ml), dried (magnesium sulphate) and evaporated. The resulting yellow solid was combined with the yellow crystals and recrystallized from ethanol to yield 6-cyano-2,3-(4'-methylcyclohexeno)chromone (4.85 g), m.p. 223°–224°. Concentration of the filtrate yielded an additional 1.1 g, m.p. 218°–222°.

Calcd for $C_{15}H_{13}NO_2$: C, 75.30; H, 5.48; N, 5.85%. Found: C, 75.10; H, 5.52; N, 5.94%.

The cyano intermediate was converted into the desired cycloalkenochromone as follows.

(c) A mixture of 6-cyano-2,3-(4'-methylcyclohexeno)chromone (3.0 g), glacial acetic acid (10 ml) and 50 percent sulphuric acid (20 ml) was heated under reflux for four hours, then cooled and added dropwise with stirring to water (100 ml). The creamy-white precipitate was filtered and dissolved in saturated sodium hydrogen carbonate solution (100 ml). The dissolved material was warmed, treated with charcoal, filtered hot and then reprecipitated with dilute hydrochloric acid (100 ml). The product was filtered and dried to yield 6-carboxy-2,3-(4'-methylcyclohexeno)chromone (3.2 g), m.p. 242°–245°.

Calcd for $C_{15}H_{14}O_4$: C, 69.75; H, 5.46%. Found: C, 69.42; H, 5.44%.

EXAMPLE 4

6-(5-(1H)-tetrazolyl-2,3-(4'-methylcyclohexeno)chromone

A mixture of sodium azide (0.72 g), ammonium chloride (0.60 g) and 6-cyano-(5-(1H)-tetrazolyl)-2,3-(4'-methylcyclohexeno)chromone (2.39 g) in dimethylformamide (20 ml) was heated at 100° for six hours. After cooling, the mixture was filtered and the filtrate was acidified to pH 2 with dilute hydrochloric acid. A yellow-brown solid was collected which was recrystallized from aqueous dimethylformamide to give 6-(5-(1H)-tetrazolyl)-2,3-(4'-methylcyclohexeno)chromone (1.75 g) m.p. 275°–276°.

Calcd for $C_{15}H_{14}N_4O_4$: C, 63.82; H, 5.00; N, 19.85%. Found: C, 63.94; H, 5.30; N, 19.23%.

EXAMPLE 5

Sodium-6-carboxy-2,3-(4'-ethylcyclohexeno)chromone (a) 6-Iodo-2,3-(4'-ethylcyclohexeno)chromone Triethylamine (40.4 g) was added dropwise to a stirred suspension of 5-iodoacetylsalicyclic acid (122.4 g) in dry chloroform (400 ml) while maintaining the temperature below 5° C. The mixture was then cooled below −10° C. and ethyl chloroformate (43.6 g) was slowly added. After fifteen minutes 1-(N-piperidino)-4-ethylcyclohexene (77.2 g) was added. After stirring at ambient temperature for 17 hours, concentrated hydrochloric acid (280 ml) was added and the mixture was refluxed for four hours. After cooling, the aqueous chloroform and layer were separated and the aqueous phase was extracted with chloroform (2×200 ml). The combined chloroform layers were washed successively with water (400 ml), 2.5 percent sodium carbonate solution (400 ml) and water (400 ml), dried (magnesium sulphate) and evaporated. The residue was triturated with cold ether to give 6-iodo-2,3-(4'-ethylcyclohexeno)chromone (23.0 g), m.p. 144°–146°.

Calcd for $C_{15}H_{15}IO_2$: C, 50,86; H, 4.27; I, 35.83%. Found: C, 50.85; H, 4.32; I, 36.18%.

(b) 6-Cyano-2,3-(4'-ethylcyclohexeno)chromone

6-Iodo-2,3-(4'-ethylcyclohexeno)chromone (50.1 g) and cuprous cyanide (13.95 g) were heated together with dimethylformamide (150 ml) for 48 hours. Insoluble material was removed by filtration and the filtrate cooled. Some product crystallized out; this was filtered and washed with cold dimethylformamide. The filtrate was poured into a solution of ferric chloride hexahydrate (30 g) in concentrated hydrochloric acid and water (90 ml) and the mixture heated on a steam bath for 30 minutes. After cooling, the mixture was extracted with ether (3×600 ml); the combined extracts were washed with 10 percent sodium bisulphite solution (5×100 ml), dried (magnesium sulphate) and concentrate. The yellow residue was triturated with cold ether and the product filtered. On recrystallization from ethanol, 6-cyano-2,3-(4'-ethylcyclohexeno)chromone (23 g), m.p. 168°–170°, was obtained.

Calcd for $C_{16}H_{15}NO_2$: C, 75.87; H, 5.87; N, 5.53%. Found: C, 75.68; H, 5.87; N, 5.66%.

The cyano intermediate was converted into the cycloalkenochromone as follows.

A solution of 6-cyano-2,3-(4'-ethylcyclohexeno)chromone (8 g) in glacial acetic acid (25 ml) and fifty percent sulphuric acid (50 ml) was heated under reflux for four hours and then poured into water (250 ml) with stirring. The light brown precipitate was filtered, washed with water, dissolved in 10 percent sodium hydrogen carbonate solution (100 ml), warmed and treated with charcoal. The solution was filtered and the filtrate acidified by the addition of dilute hydrochloric acid. The resulting precipitate was filtered and dried to give sodium 6-carboxy-2,3-(4'-ethylcyclohexeno)chromone (8 g), m.p. 220°–223° C.

Calcd for $C_{16}H_{15}O_4Na$: C, 65.43; H, 5.11%. Found: C, 65.44; H, 5.51%.

EXAMPLE 6

Sodium 6-(5-(1H)-tetrazolyl)-2,3-(4'-ethylcyclohexeno)chromone

Ammonium chloride (3.0 g) and sodium azide (3.6 g) were added to 6-cyano-2,3-(4'-ethylcyclohexeno)chromone (12.9 g) dissolved in dimethylformamide (100 ml) and the mixture was heated and stirred at 100° for three hours. After cooling, inorganic material was removed by filtration and the filtrate was added dropwise to water (100 ml) with stirring to give a pale yellow solution. On acidification to pH 2 with concentrated hydrochloric acid, a pale yellow precipitate formed which was collected and dissolved in sodium hydrogen carbonate solution. Addition of concentrated hydrochloric acid to the resulting solution gave the sodium salt of 6-(5-(1H)-tetrazolyl-2,3-(4'-ethylcyclohexeno)chromone (12 g) as a yellow solid, m.p. 251°–255°.

Calcd for $C_{16}H_{15}N_4O_2Na$: C, 60.85; H, 5.44; N, 18.91% Found: C, 60.36; H, 5.09; N, 17.64%

EXAMPLE 7

6-Carboxy-2,3-(4'-carboxycyclohexeno)chromone (a) 6-Iodo-2,3-(4'-ethoxycarbonylcyclohexeno)chromone Ethyl chloroformate (21.8 g) was added slowly to the triethylamine salt of 5-iodosalicylic acid (prepared from triethylamine (20.2 g) and the acid (61.2 g) in chloroform while maintaining the temperature in the range −10° to −5°. Fifteen minutes after the completion of the addition, 1-(N-piperidino)-4-ethoxycarbonylcyclohexene (52.3 g) was added dropwise, keeping the temperature about −5°. The reaction mixture was then stirred for 18 hours at room temperature. Concentrated hydrochloric acid (140 ml) was added and the mixture was heated under reflux for 5½ hours. On cooling, the phases were separated and the aqueous phase was extracted with chloroform (100 ml). The organic phases were combined and washed successively with water, sodium carbonate solution and water, dried (magnesium sulphate) and evaporated. A pale yellow precipitate was obtained on adding ice-cold ether to the oily residue which was filtered to yield 6-iodo-2,3-(4'-ethoxycarbonylcyclohexeno)chromone (13 g), mp. 125°–128°.

Calcd for $C_{16}H_{15}IO_4$: C, 48.26; H, 3.80; I, 31.87%. Found: C, 46.29; H, 3.65; I, 32.70%.

(b) 6-Cyano-2,3-(4'-ethoxycarbonylcyclohexeno)chromone

A mixture of 6-iodo-2,3-(4'-ethoxycarbonylcyclohexeno)-chromone (5.6 g) and cuprous cyanide (1.4 g) in dimethylformamide (15 ml) was heated under reflux for 36 hours. The hot solution was filtered and the residue was extracted with hot dimethylformamide (2×15 ml). On cooling, the extracts yielded 6-cyano-2,3-(4'-ethoxycarbonylcyclohexeno)chromone (2.8 g) m.p. 174°–176° as pale yellow crystals.

Calcd for $C_{17}H_{15}NO_4$: C, 68.67; H, 5.08; N, 4.71%. Found: C, 67.82; H, 5.16; N, 5.12%.

The cyano intermediate was converted into the cycloalkenochromone as follows:

Concentrated sulphuric acid (5 ml) and water (5 ml) were added to 6-cyano-2,3-(4'-ethoxycarbonylcyclohexeno)-chromone (1.5 g) dissolved in glacial acetic acid (5 ml) and the solution heated under reflux for four hours. During heating, a white precipitate formed which was filtered and washed successively with glacial acetic acid and water to give 6-carboxy-2,3-(4'-carboxycyclohexeno)chromone (1.32 g) m.p. 359°–363°.

Calcd for $C_{15}H_{12}O_6$: C, 62.50; H, 4.20%. Found: C, 61.56; H, 4.39%.

EXAMPLE 8

6-(5-(1H)-tetrazolyl)-2,3-(4'-ethoxycarbonylcyclohexeno)chromone

A mixture of sodium azide (0.29 g), ammonium chloride (0.24 g) and 6-cyano-2,3-(4'-ethoxycarbonylcyclohexeno)-chromone (1.18 g) in dimethylformamide (8 ml) was heated with stirring at 100° for three hours. The hot mixture was filtered from inorganic materials and the filtrate added dropwise with stirring to water (100 ml). The precipitate that formed on adding dilute hydrochloric acid was filtered off and dissolved in sodium hydrogen carbonate solution. The carbonate solution was extracted with ethyl acetate and the organic extract discarded. Acidification yielded a yellow precipitate of 6-(5-(1H)-tetrazolyl)-2,3-(4'-ethoxycarbonylcyclohexeno)chromone (0.82 g), m.p. 252°–255°.

Calcd for: $C_{17}H_{16}N_4O_4$: C, 59.99; H, 474; N, 16.46%. Found: C, 58.65; H, 4.68; N, 17.12%.

EXAMPLE 9

6-Carboxy-2,3-(4'-isopropylcyclohexeno)chromone (a) 6-Iodo-2,3-(4'-isopropylcyclohexeno)chromone A suspension of 5-iodoacetylsalicylic acid triethylamine salt [prepared from the acid (30.6 g) and triethylamine] in chloroform (100 ml) was cooled to below 10° and treated with ethyl chloroformate (10.9 g). Fifteen minutes after the completion of the addition, 1-(N-piperidino)-4-isopropylcyclohexene (25.5 g) was added dropwise while the temperature was maintained between −5° and 0°. After stirring for four hours at room temperature, concentrated hydrochloric acid (70 ml) was added and the two-phase mixture was heated under reflux for four hours. After cooling, the phases were separated and the aqueous layer was extracted with chloroform (50 ml). The combined organic phases were washed successively with water, sodium carbonate solution and water, and then dried (magnesium sulphate) and concentrated. The resulting semi-solid was triturated with ice-cold ether to yield 6-iodo-2,3-(4'-isopropylcyclohexeno)chromone (8.2 g), m.p. 155°–157°.

Calcd for $C_{16}H_{17}IO_2$: C, 52.19; H, 4.65; I, 34.47%. Found: C, 51.95; H, 4.48; I, 34.29%.

(b) 6-Cyano-2,3-(4'-isopropylcyclohexeno)chromone

6-Iodo-2,3-(4'-isopropylcyclohexeno)chromone (7.73 g) and cuprous cyanide (2.1 g) were heated together in dimethylformamide (23 ml) for 48 hours. After cooling, the reaction mixture was poured into a solution containing ferric chloride hexahydrate (3.75 g), concentrated sulphuric acid (11 ml) and water (11 ml) and warmed in a water bath for 30 minutes. After cooling, the resulting brown suspension was extracted with ether and the ethereal extracts were washed with 10 percent sodium bisulphite solution and dried (magnesium sulphate). Removal of the ether yielded a yellow solid which was recrystallized from ethanol to yield 6-cyano-2,3-(4'-isopropylcyclohexeno)chromone (4.35 g) as yellow crystals, m.p. 165°–168°.

Calcd for $C_{17}H_{17}NO_2$: C, 76.38; H, 6.41; N, 5.24%. Found: C, 76.04; H, 6.35; N, 5.25%.

The cyano intermediate was converted into the cycloalkenochromone as follows.

Fifty percent sulphuric acid (20 ml) was added to 6-cyano-2,3-(4'-isopropylcyclohexeno)chromone (3.0 g) in glacial acetic acid (10 ml) and the mixture was heated under reflux for four hours. After cooling, the reaction mixture was added dropwise to water (100 ml) and the resulting precipitate filtered, dissolved in warm sodium hydrogen carbonate solution, treated with charcoal, filtered and finally acidified with dilute hydrochloric acid. The product was collected and recrystallized from aqueous acetic acid to give 6-carboxy-2,3-(4'-isopropylcyclohexeno)chromone (2.85 g), m.p. 235°–240°.

Calcd for $C_{17}H_{18}O_4$: C, 71.31; H, 6.34%. Found: C, 70.25; H, 6.24%.

EXAMPLE 10

6-(5-(1H)-tetrazolyl)-2,3-(4'-isopropylcyclohexeno)chromone

A mixture of sodium azide (0.29 g), ammonium chloride (0.24 g) and 6-cyano-2,3-(4'-isopropylcyclohexeno)chromone (1.07 g) in dimethylformamide (8 ml) was heated at 90°–100° for three hours. The hot mixture was filtered and the filtrate added dropwise with stirring to water (100 ml), which was then acidified by the addition of dilute hydrochloric acid (2 ml). The resulting yellow precipitate was filtered and partially dissolved in sodium hydrogen carbonate solution and the suspension extracted with ethyl acetate. The aqueous phase was separated and acidified with dilute hydrochloric acid to give 6-(5-(1H)-tetrazolyl)-2,3-(4'-isopropylcyclohexeno)chromone (1.25 g) as a yellow solid, m.p. 269°–270°.

Calcd for $C_{17}H_{18}N_4O_2$: C, 65.79; H, 5.85; N, 18.05%. Found: C, 64.21; H, 5.77; N, 17.78%.

EXAMPLE 11

6-Carboxy-2,3-cycloheptenochromone (a) 6-Iodo-2,3-cycloheptenochromone

Triethylamine (5.06 g) was added dropwise with stirring to a suspension of 5-iodoacetylsalicylic acid in chloroform (50 ml) while maintaining the temperature below 5°. The mixture was then cooled and maintained below −5° and ethyl chloroformate (5.43 g) added. 1-(N-Piperidino)cycloheptene (8.95 g) was added with the temperature maintained between −5° and −10°. The reaction mixture was left in the cooling bath for 30 minutes during which time it warmed gradually to room temperature and was then stirred for four hours. Concentrated hydrochloric acid (35 ml) was then added and the mixture heated under reflux for four hours. After cooling, the aqueous layer was separated and discarded, the chloroform solution was washed successively with water (2×50 ml), 2 percent sodium carbonate solution (2×50 ml) and water (2×50 ml), and dried (magnesium sulphate). Evaporation yielded a yellow solid which was washed repeatedly with ether until white, to yield 6-iodo-2,3-cycloheptenochromone (3.2 g), m.p. 118°–120°.

Calcd for $C_{14}H_{13}IO_2$: C, 49.43; H, 3.85; I, 37.31%. Found: C, 49.44; H, 3.67; I, 36.99%.

(b) 6-Cyano-2,3-cycloheptenochromone

6-Cyano-2,3-cycloheptenochromone (32.3 g) and cuprous cyanide (8.95 g) were dissolved in dimethylformamide (100 ml) and heated under reflux for 48 hours. The flask was cooled slightly and the residual solid removed by filtration. The filtrate was poured into a solution of anhydrous ferric chloride (12 g) in concentrated hydrochloric acid (60 ml) and water (60 ml), warmed on a water bath for 30 minutes, cooled and extracted with ether (3×400 ml). The combined ethereal extracts were washed with 10 percent sodium bisulphite solution (4×200 ml), dried over magnesium sulphate and concentrated to give 9.23 g of a product, m.p. 165°–169°. Recrystallization from ethanol yielded 6-cyano-2,3-cycloheptenochromone (4.35 g) m.p. 170°–172°.

Calcd for $C_{15}H_{13}NO_2$: C, 75.30; H, 5.48; N, 5.85%. Found: C, 74.77; H, 5.71; N, 5.91%.

The cyano intermediate was converted into the cycloalkenochromone as follows:

A solution of 6-cyano-2,3-cycloheptenochromone (3.4 g), in glacial acetic acid (15 ml) and 50 percent sulphuric acid (25 ml) was heated under reflux for four hours. After cooling, the solution was poured with stirring into water (150 ml) and the resulting brown precipitate was filtered. Recrystallization from aqueous acetic acid (charcoal) yielded 6-carboxy-2,3-cycloheptenochromone (2.4 g) m.p. 218°–220°.

Calcd for $C_{15}H_{14}O_4$: C, 68.28; H, 5.73%. Found: C, 69.57; H, 5.75%.

EXAMPLE 12

6Carboxy-2,3-cyclooctenochromone

6-Iodo-2,3-cyclooctenochromone

5-Iodoacetylsalicylic acid (61.2 g) was suspended in chloroform (200 ml) and stirred. The flask was cooled in an ice-bath and triethylamine (20.24 g) was added dropwise, maintaining the temperature below 5° C. The ice-bath was replaced by one containing acetone and solid carbon dioxide, and ethyl chloroformate was slowly added while maintaining the internal temperature below −5°. The cooling mixture was removed and the contents of the flask were allowed to warm to 0°. The flask was then cooled again to below −10° and 1-(N-piperidino)cycloocten (38.6 g) was added dropwise, keeping the temperature between −5° and −10°.

The reaction mixture was left in the cooling bath for 30 minutes during which time it warmed up gradually to room temperature and then stirred for 3½ hours. Concentrated hydrochloric acid (140 ml) was added and the mixture heated under reflux for four hours. After cooling, the chloroform layer was separated, washed successively with water (2×250 ml), 2 percent sodium carbonate solution (2×250 ml), and water, dried over magnesium sulphate and concentrated to give a brown oil from which a yellow solid separated. The solid was collected and washed with ether to give a white product, 6-iodo-2,3-cyloocetenochromone (27.1 g), m.p. 95°–97°.

Calcd for $C_{15}H_{15}IO_2$: C, 50.86; H, 4.27; I, 35.83%. Found: C, 50.67; H, 3.95; I, 35.75%.

(b) 6-Cyano-2,3-cyclooctenochromone

6-Iodo-2,3-cyclooctenochromone (24 g) and cuprous cyanide (6.4 g) were heated together in dimethylformamide for 65 hours. The flask was cooled slightly, insoluble material was removed by filtration, and the filtrate was poured into a solution of anhydrous ferric chloride (10.9 g) in concentrated hydrochloric acid (40 ml) and distilled water (40 ml). The mixture was heated on a steam bath for 30 minutes, allowed to cool and extracted with ether (3×250 ml).

The combined ethereal extracts were washed with 10 percent sodium bisulfite solution (5×50 ml), dried (magnesium sulfate) and concentrated to give a solid that was recrystallized from ethanol to give 6-cyano-2,3-cyclooctenochromone (13.8 g), m.p. 122°–124°.

Calcd for $C_{16}H_{15}NO_2$: C, 75.87; H, 5.97; N, 5.53%. Found: C, 73.44; H, 5.87; N, 6.10%.

The cyano intermediate was converted into the cycloalkenochromone as follows.

A solution of 6-cyano-2,3-cyclooctenochromone (5.06 g) in glacial acetic acid and fifty percent sulphuric acid (40 ml) was heated under reflux for four hours. After cooling, the reaction mixture was added slowly with stirring to distilled water (250 ml). A white precipitate formed which was filtered, washed with water and dried. Recrystallization from aqeous acetic acid afforded 6-carboxy-2,3-cyclooctenochromone (4.33 g), m.p. 262°–264° C.

Calcd for $C_{16}H_{16}O_4$: C, 69.21; H, 6.20%. Found: C, 70.46; H, 5.93%.

EXAMPLE 13

6-(5-(1H)-tetrazolyl)-2,3-cyclooctenochromone

A mixture of sodium azide (0.85 g), ammonium chloride (0.75 g) and 6-cyano-2,3-cyclooctenochromone (3.04 g) was heated with stirring at 100° in dimethylformamide (25 ml) for three hours. After cooling, inorganic solids were filtered and the filtrate was added dropwise with stirring to distilled water (250 ml) and then acidified was dilute hydrochloric acid to pH 2. The precipitate was filtered, washed with water and dried. Recrystallization from dimethylformamide gave 6-(5-(1H)-tetrazolyl)-2,3-cyclooctenochromone (1.94 g), m.p. 295°–296°.

Calcd for $C_{16}H_{16}N_4O_2$: C, 63.36; H, 5.67; N, 19.71%. Found: C, 64.79; H, 5.71; N, 18.46%.

EXAMPLE 14

6-Carboxy-2,3-cyclopentenochromone (a) 6-Iodo-2,3-cyclopentenochromone, m.p. 134°–136°, was prepared from 5-iodoacetylsalicylic acid and 1-(N-piperidino)cyclopentene according to the procedure described in Example 1(a).

Calcd for $C_{12}H_9IO_2$: C, 46.18; H, 2.91; I, 40.66%. Found: C, 45.86; H, 2.75; I, 40.45%.

(b) 6-Cyano-2,3-cyclopentenochromone, m.p. 194°–196°, was prepared from 6-iodo-2,3-cyclopentenochromone according to the procedure described in Example 1(b).

Calcd for $C_{13}H_9NO_2$: C, 73.92; H, 4.30; N, 6.63%. Found: C, 73.64; H, 4.28; N, 6.80%.

The cyano intermediate was converted into the cycloalkenochromone (m.p. 278°–280°) according to the procedure described in Example 1(c).

Calcd for $C_{13}H_{10}O_4$: C, 67.82; H, 4.38%. Found: C, 67.66; H, 4.46%.

EXAMPLE 15

6-Carboxy-2,3-(4'-benzyloxycyclohexeno)chromone (a) 6-Iodo-2,3-(4'-benzyloxycyclohexeno)chromone, m.p. 92°–94°, was prepared from 5-iodoacetylsalicylic acid and 1-(N-piperidino)-4-benzyloxy-cyclohexene according to the procedure described in Example 1(a).

Calcd for $C_{20}H_{17}IO_3$: C, 55.57; H, 3.96; I, 29.36%. Found: C, 55.40; H, 4.24; I, 29.45%.

(b) 6-Cyano-2,3-(4'-benzyloxycyclohexeno)chromone, m.p. 146°–148°, was prepared from 6-iodo-2,3-(4'-benzyloxycyclohexeno)chromone according to the procedure described in Example 1(b).

Calcd for $C_{21}H_{17}NO_3$: C, 76.12; H, 5.17; N, 4.23%. Found: C, 76.30; H, 5.24; N, 4.33%.

The cyano intermediate was converted into the cycloalkenochromone (m.p. 202°–205°) according to the procedure described in Example 1(c).

Calcd for $C_{21}H_{18}O_5$: C, 71.99; H, 5.18%. Found: C, 73.04; H, 4.68%.

EXAMPLE 16

6-(5-(1H)-Tetrazolyl)-2,3-(4'-benzyloxycyclohexeno)-chromone

The cycloalkenochromone (m.p. 290°–291°) was prepared from 6-cyano-2,3-(4'-benzyloxycyclohexeno)-chromone by the procedure described in Example 2(a).

Calcd for $C_{21}H_{18}N_4O_3$: C, 67.37; H, 4.85; N, 14.97%. Found: C, 66.64; H, 4.86; N, 15.00%.

EXAMPLE 17

6-Methylthio-2,3-(4'-ethoxycarbonylcyclohexeno)chromone

The cycloalkenochromone (m.p. 125°–128°) was prepared from 5-methylthioacetylsalicylic acid and 1-(N-piperidino)-4-ethoxycarbonylcyclohexene by the procedure described in Example 1(a).

Calcd for $C_{17}H_{18}O_4S$: C, 64.14; H, 5.70; S, 10.05%. Found: C, 63.66; H, 6.02; S, 10.10%.

EXAMPLE 18

6-Methylthio-2,3-(4'-carboxycyclohexeno)chromone

The cycloalkenochromone, (m.p. 226°–229°) was prepared by hydrolysis with sodium hydroxide solution as follows.

6-Methylthio-2,3-(4'-ethoxycarbonylcyclohexeno)-chromone (3.0g) was dissolved in warm ethanol (50 ml). Sodium hydroxide solution (10%, 5 ml) was added dropwise and the solution heated to reflux for 2 hours and then cooled to 0°. The sodium salt was filtered, washed with a little ethanol, and dried. It was then dissolved in water (100 ml) and the solution acidified with dilute hydrochloric acid. The precipitate was filtered, washed with water and dried to yield 6-methythio-2,3-(4'-carboxycyclohexeno)chromone (2.0 g), m.p. 226°–229°.

Calcd for $C_{15}H_{14}O_4S$: C, 62.06; H, 4.86; S, 11.02%. Found: C, 61.67; H, 5.03; S, 10.87%.

EXAMPLE 19

6-Methylsulfinyl-2,3-(4'-carboxycyclohexeno)chromone

The cycloalkenochromone, (m.p. 246°–248°) was prepared by oxidation with sodium metaperiodate as follows.

6-Methylthio-2,3-(4'-carboxycyclohexeno)chromone (290 mg) was dissolved in sodium hydrogen carbonate solution and a solution of sodium periodate (227 mg) added at 0°. After stirring at 0° for 60 hours, the solution was filtered and added to dilute hydrochloric acid (20 ml). The crystals which separated were filtered, washed with water and dried to yield 6-methylsulphinyl-2,3-(4'-carboxycyclohexeno)-chromone (240 mg) m.p. 246°–248°.

Calcd for $C_{15}H_{14}O_5S$: C, 58.81; H, 4.61; S, 10.47%. Found: C, 58.67; H, 4.49; S, 10.53%.

EXAMPLE 20

6-Methylsulfonyl-2,3-(4'-carboxycyclohexeno)chromone

The cycloalkenochromone, (m.p. 243°–244°) was prepared by oxidizing 6-methylthio-2,3-(4'-carboxycyclohexeno)chromone with hydrogen peroxide in glacial acetic acid according to the procedure described in Example 32.

Calcd for $C_{15}H_{14}O_6S$: C, 55.90; H, 4.38; S, 9.95%. Found: C, 55.72; H, 4.44; S, 9.85%.

EXAMPLE 21

6-Carboxy-2,3-(4'-methoxycyclohexeno)chromone (a) 6-Iodo-2,3-(4'-methoxycyclohexeno)chromone, m.p. 149°–150°, was prepared from 5-iodoacetylsalicylic acid and 1-(N-piperidino)-4-methoxycyclohexene according to the procedure described in Example 1(a).

Calcd for $C_{14}H_{13}IO_3$: C, 47.21; H, 3.68; I, 35.63%. Found: C, 46.15; H, 3.96; I, 36.05%.

(b) 6-Cyano-2,3-(4'-methoxycyclohexeno)chromone, m.p. 138°–140°, was prepared from 6-iodo-2,3-(4'-methoxycyclohexeno)chromone according to the procedure described in Example 1(b).

Calcd for $C_{15}H_{13}NO_3$: C, 70.58; H, 5.13; N, 5.49%. Found: C, 70.68; H, 5.00; N, 5.53%.

The cyano intermediate was converted into the cycloalkenochromone (m.p. 217°–219°) according the procedure described in Example 1(c).

Calcd for $C_{15}H_{14}O_5$: C, 65.59; H, 5.15%. Found: C, 65.58; H, 5.11%.

EXAMPLE 22

6-(5-(1H)-Tetrazolyl)-2,3-(4'-methoxycyclohexeno)-chromone

The cycloalkenochromone, (m.p. 268°–270°) was prepared from 6-cyano-2,3-(4'-methoxycyclohexeno)-chromone according to the procedure described in Example 2.

Calcd for $C_{15}H_{14}N_4O_3$: C, 60.39; H, 4.73; N, 18.78%. Found: C 60.32; H, 4.79; N, 18.08%.

EXAMPLE 23

7-(5-(1H)-tetrazolyl-2,3-cyclopentenochromone

7-Iodo-2,3-cyclopentenochromone, m.p. 246°–248°, was prepared from 4-iodoacetylsalicylic acid and 1-(N-piperidino)cyclopentene according to the procedure described in Example 1(a) and converted to 7-cyano-2,3-cyclopentenochromone using cuprous cyanide. The cyano compound was converted to 7-carboxy-2,3-cyclopentenochromone and 7-(5-(1H)-tetrazolyl)-2,3-cyclopentenochromone using the procedures described in Example 1(c) and 2 respectively.

EXAMPLE 24

7-Carboxy-2,3-cyclohexenochromone (a) 7-Iodo-2,3-cyclohexenochromone, m.p. 194°–196°, was prepared from 4-iodoacetylsalicylic acid and 1-(N-pyrrolidino)cyclohexene according to the procedure described in Example 1(a).

Calcd for $C_{13}H_{11}IO_2$: C, 47.87; H, 3.40; I, 38.92%. Found: C, 48.10; H, 3.16; I, 39.34%.

(b) 7-Cyano-2,3-cyclohexenochromone, m.p. 188°–190°, was prepared from 7-iodo-2,3,-cyclohexenochromone and cuprous cyanide according to the procedure described in Example 1(b).

Calcd for $C_{14}H_{11}NO_2$: C 74.65; H, 4.92; N, 6.22%. Found: C, 73.91; H, 5.21; N, 5.07%.

The cyano intermediate was converted into the cycloalkenochomone, (m.p. 276°–278°) according to the procedure described in Example 1(c).

Calcd for $C_{14}H_{12}O_4$: C, 68.84; H, 4.95%. Found: C, 68.75; H, 5.02%.

EXAMPLE 25

7(5-(1H)-tetrazolyl)-2,3-cyclohexenochromone

The cycloalkenochromone, (m.p. 276°–278°) was prepared from 7-cyano-2,3-cyclohexenochromone according to the procedure described in Example 2.

Calcd for $C_{14}H_{12}N_4O_2$: C, 62.68; H, 4.51; N, 20.89%. Found: C, 62.19; H, 4.68; N, 20.45%.

EXAMPLE 26

7-Carboxy-2,3-(4'-ethylcyclohexeno)chromone (a) 7-Iodo-2,3-(4'-ethylcyclohexeno)chromone, m.p. 99°–101°, was prepared from 4-iodoacetylsalicylic acid and 1-(N-pyrrolidino)-4-ethylcyclohexene according to the procedure described in Example 1(a).

Calcd for $C_{15}H_{15}IO_2$: C, 50.86; H, 4.27; I, 35.83%. Found: C, 50.93; H, 4.26; I, 35.76%.

(b) 7-Cyano-2,3-(4'-ethylcyclohexeno)chromone, m.p. 161°–163° was prepared from 7-iodo-2,3-(4'-ethylcyclohexeno)chromone and cuprous cyanide according to the procedure described in Example 1(b).

Calcd for $C_{16}H_{15}NO_2$: C, 75.87; H, 5.97; N, 5.53%. Found: C, 75.81; H, 6.10; N, 5.48%.

The cyano intermediate was converted into the cycloalkenochromone, (m.p. 252°–254°) according to the procedure described in Example 1(c).

Calcd for $C_{16}H_{16}O_4$: C, 70.57; H, 5.92%. Found: C, 70.53; H, 5.98%.

EXAMPLE 27

7-(5-(1H)-tetrazolyl)-2,3-(4'-ethylcyclohexeno)chromone

The cycloalkenochromone, (m.p. 266°–268°), was prepared from 7-cyano-2,3-(4'-ethylcyclohexeno)chromone and sodium azide according to the procedure described in Example 2.

Calcd for $C_{16}H_{16}N_4O_2$: C, 64.85; H, 5.44; N, 18.91%. Found: C, 64.90; H, 5.39; N, 19.16%.

EXAMPLE 28

6-Carboxy-2,3-(4', 4'-dimethylcyclohexeno)chromone (a) 6-Iodo-2,3-(4',4'-dimethylcyclohexeno)chromone, m.p. 184°–185°, was prepared from 5-iodoacetylsalicylic acid and 1-(N-pyrrolidino)-4,4-dimethylcyclohexene according to the procedure described in Example 1(a).

Calcd for $C_{15}H_{15}IO_2$: C, 50.86; H, 4.27; I, 35.83%. Found: C, 50.93; H, 4.34; I, 35.66%.

(b) 6-Cyano-2,3-(4',4'-dimethylcyclohexeno)chromone, m.p. 186°–188°, was prepared from 6 -iodo-2,3-(4',4'-dimethylcyclohexeno)chromone and cuprous cyanide according to the procedure described in Example 1(b).

Calcd for $C_{16}H_{15}NO_2$: C, 75.80; H, 5.97; N, 5.53%. Found: C, 75.93; H, 5.89%; N, 5.53%.

The cyano intermediate was converted into the cycloalkenochromone (m.p. 239°–243°) according to the procedure described in Example 1(c).

Calcd for $C_{16}H_{16}O_4$: C, 70.57; H, 5.92%. Found: C, 70.51; H, 6.04%.

EXAMPLE 29

6-(5-(1H)-tetrazolyl)-2,3-(4',4'-dimethylcyclohexeno)-chromone

The cycloalkenochromone (m.p. 292°, decomposition) was prepared from 6-cyano-2,3-(4',4'-dimethylcyclohexeno)chromone and sodium azide by the procedure described in Example 2.

Calcd for $C_{16}H_{16}N_4O_2$: C, 64.85; H, 5.44; N, 18.91%. Found: C, 64,92; H, 5.54; N, 18.80%.

EXAMPLE 30

6-Carboxy-2,3-(4'-methyl-4'-phenylcyclohexeno)chromone (a) 6-Iodo-2,3-(4'-methyl-4'-phenylcyclohexeno)-chromone O-Acetyl-5-iodosalicyclic acid (10.7 g) was added to a solution of 1,1'-carbonyl-diimidazole (5.7 g) in dry chloroform (20 ml) stirred under dry nitrogen. After 30 minutes, 4-methyl-4-phenyl-1-(N-pyrrolidino)cyclohexene (7.8 g) was added. The resulting solution was stirred 25 hours, washed successively with water, 10% sodium hydroxide solution, water, dilute hydrochloric acid and water, then dried over sodium sulphate. The chloroform was removed and the residue washed with diethyl ether to afford 6-iodo-2,3-(4'-methyl-4'-phenylcyclohexeno)chromone (5.8 g, 44%), as a white solid, m.p. 160°–162°.

Calcd for $C_{20}H_{17}IO_2$: C, 57.71; H, 4.12; I, 30.49%. Found: C, 57.63; H, 3.98; I, 30.21%.

(b) 6-Cyano-2,3-(4′-methyl-4′-phenylcyclohexeno)-chromone (m.p. 177°–178°) was prepared from 6-iodo-2,3,-(4′-methyl-4′-phenylcyclohexeno)chromone and cuprous cyanide according to the procedure described in Example 1(b).

Calcd for $C_{21}H_{17}NO_2$: C, 79.99; H, 5.43; N, 4.44%. Found: C, 79.90; H, 5.61; N, 4.50%.

The cyano intermediate was converted into the cycloalkenochromone (m.p. 270°–272°) by hydrolysis according to the procedure described in Example 1(c).

Calcd for $C_{21}H_{18}O_4$: C, 75.45; H, 5.42%. Found C, 75.24; H, 5.54%.

EXAMPLE 31

6-(5-(1H)-tetrazolyl)-2,3-(4′-methyl-4′-phenylcyclohexeno)chromone

The cycloalkenochromone (m.p. 281°–281.5°) was prepared from 6-cyano-2,3-(4′-methyl-4′-phenylcyclohexeno)chromone and sodium azide according to the procedure described in Example 2.

Calcd for $C_{21}H_{18}N_4O_2$: C, 68.65; H, 5.21; N, 15.25%. Found: C, 68.81; H, 5.27; N, 15.35%.

EXAMPLE 32

6-Carboxy-2,3-(4′-ethylcyclohexeno)thiochromone-1,1-dioxide

A mixture of 6-carboxy-2,3-(4′-ethylcyclohexeno)thiochromone (350 mg) and hydrogen peroxide (0.8 ml, 30%) in acetic acid (30 ml) was heated to reflux for two hours. The solution was then filtered, diluted with an equal volume of water, and allowed to cool. The resulting crystals were collected, washed with water and dried to yield 6-carboxy-2,3-(4′-ethylcyclohexeno)thiochromone-1,1-dioxide (286 mg) as cream flakes, m.p. 217°–219°.

Calcd for $C_{16}H_{16}O_5S$: C, 59.98; H, 5.03; S, 10.01%. Found: C, 59.47; H, 4.78; S, 10.81%.

EXAMPLE 33

6-Carboxy-2,3-(4′-ethylcyclohexeno)thiochromone (a) 5-Iodoacetylthiosalicylic acid A solution of 5-iodoanthranilic acid (71.1 g; 0.272 mole), sodium hydroxide (11.5 g; 0.275 mole) and sodium nitrite (18.75 g; 0.275 mole) in water (325 ml) was added slowly with stirring to a mixture of concentrated hydrochloric acid (75 ml) and ice (100 g) while the temperature was maintained between 0° and 5° by external cooling and by the addition of ice. After completion of the addition of the nitrite solution, the mixture was stirred for an additional 30 minutes and adjusted to pH 7 with dilute sodium hydroxide solution and potassium acetate. The cold diazonium mixture was added to a vigorously stirred solution of potassium ethyl xanthate (125 g; 0.775 mole) in water (400 ml) preheated to 75°–80°. When the evolution of nitrogen ceased, the reaction mixture was cooled and acidified to pH 3 with concentrated hyrochloric acid. After decanting the aqueous phase, the resulting sludge was dissolved in 10 percent sodium hydroxide solution (200 ml) and heated on a steam bath for two hours. The solution was cooled, filtered, acidified to pH 4–5 with concentrated hydrochloric acid, and the solid collected, washed and dried. The resulting disulfide was refluxed for 16 hours with zinc dust (25 g) in glacial acetic acid (750 ml). The solid was collected, washed with cold water, digested with concentrated hydrochloric acid for 30 minutes, filtered, washed with water and dried to give 5-iodothiosalicyclic acid (61.3 g), m.p. 208°–210°. Treatment of 5-iodothiosalicyclic acid (60 g) with acetic anhydride (300 ml) and concentrated sulfuric acid (1 ml) at 100° for one hour yielded 5-iodoacetylthiosalicylic acid (35.1 g), m.p. 163°14 165°.

(b) 6-Iodo-2,3-(4′-ethylcyclohexeno)thiochromone

Triethylamine (7.0 ml, 0.05 mole) was slowly added to a stirred suspension of 5-iodoacetylthiosalicylic acid (16.1 g, 0.05 mole) in dry chloroform (50 ml) between 0° and 5°. The resulting solution was cooled to −15° and ethyl chloroformate (4.8 ml, 0.05 mole) was added at a rate to maintain the temperature below −10°. Ten minutes after the addition of the ester, 4-ethyl-1-(N-pyrrolidino)cyclohexene (8.95 g, 0.05 mole) was added dropwise to the cooled solution, keeping the temperature below −10°. It was then allowed to return to normal, and stirring was continued for four hours. Concentrated hydrochloric acid (35 ml) was then added and the mixture was heated under reflux for four hours. It was then cooled and the organic layer was separated, washed successively with water, 2% aqueous sodium carbonate, and water again, and then dried (MgSO$_4$). The chloroform was removed under reduced pressure and the residual thiochromone was triturated with ether and collected as a cream solid (8.1 g, 44%), m.p. 129°–30° (EtOH).

Calcd for $C_{15}H_{15}IOS$: C, 48.66; H, 408; I, 34.28; S, 8.66%. Found: C, 48.79; H, 3.94; I, 34.30; S, 8.74%.

(c) 6-Cyano-2,3-(4′-ethylcyclohexeno)thiochromone

A solution of 6-iodo-2,3-(4′-ethylcyclohexeno)thiochromone (7.8 g, 0.021 mole) in dimethylformamide (50 ml) containing cuprous cyanide (2.1 g; 0.0225 mole) was heated under reflux for three hours. The resulting mixture was heated at 100° for 30 minutes with a solution of ferric chloride (4.5 g) in hydrochloric acid (1:1. 27 ml), and then cooled and extracted with chloroform (3×100 ml). The combined organic extracts were washed with water (25 ml) saturated sodium hydrogen carbonate solution (25 ml), 10% sodium bisulfite solution (25 ml) and water (25 ml) and then dried (MgSO$_4$). The solution was then concentrated under reduced pressure to give a fawn solid. Crystallization from ethanol yielded 6-cyano-2,3-(4′-ethylcyclohexeno)thiochromone (5.2 g) as off-white needles, m.p. 207°–209°.

Calcd for $C_{16}H_{15}NOS$: C, 71.36; H, 5.61; N, 5.20; S, 11.88%. Found: C, 70.84; H, 5.77; N, 5.31; S, 12.34%.

The cyano intermediate was converted into the cycloalkenochromone as follows. The cyano compound (2.0 g) was heated under reflux with a mixture of glacial acetic acid (30 ml), water (10 ml) and concentrated sulphuric acid (10 ml) for two hours and the solution was then poured into water (150 ml). The off-white precipitate was filtered, washed with water, and dried. Crystallization from acetone (charcoal) yielded 6-carboxy-2,3-(4′-ethylcyclohexeno)thiochromone (1.1 g) as a cream solid, m.p. 240°–242°.

Calcd for $C_{16}H_{16}O_3S$: C, 66.64; H, 5.59; S, 11.12%. Found: C, 66.39; H, 5.43; S, 11.17%.

EXAMPLE 34

6-(5-(1H)-tetrazolyl)-2,3-cyclohexenothiochromone

6-Iodo-2,3-cyclohexenothiochromone, m.p. 131°–132°, was prepared from 5-iodoacetylthiosalicyclic acid and 1-(N-pyrrolidino)cyclohexene and converted to 6-cyano-2,3-cyclohexenothiochromone, m.p.

213°–215° using cuprous cyanide according to the procedure described in 1(a) and 1(b) respectively. The cyano compound was converted by reaction with sodium azide to the desired cycloalkenochromone, according to the procedure described in Example 2.

EXAMPLE 35

6-(5-(1H)-tetrazolyl)-2,3-(4'-ethylcyclohexeno)thiochromone

The cycloalkenochromone, (m.p. 262°–264° decomposition) was prepared from 6-cyano-2,3-(4'-ethylcyclohexeno)thiochromone and sodium azide according to the procedure described in Example 2.

Calcd for $C_{16}H_{16}N_4OS$: C, 61.51; H, 5.16; N, 17.94; S, 10.26%. Found: C, 61.39; H, 5.31; N, 17.91; S, 10.37%.

EXAMPLE 36

6-(5-(1H)-tetrazolyl)-2,3-(4'-ethylcyclohexeno)thiochromone-1,1-dioxide

The cycloalkenochromone, (m.p. 199°–201° decomposition) was prepared by oxidation of 6-(5-(1H)-tetrazolyl)-2,3-(4'-ethylcyclohexeno)thiochromone with hydrogen peroxide in glacial acetic acid, according to the procedure described in Example 32.

Calcd for $C_{16}H_{16}N_4O_3S$: C, 55.80; H, 4.68; N, 16.27; S, 9.31%. Found: C, 55.33; H, 4.62; N, 15.84; S, 9.17%.

EXAMPLE 37

7-carboxy-2,3-cyclohexenothiochromone (a) The S-acetyl-4-iodothiosalicylic acid, m.p. 184°–186°, was prepared from 4-iodoanthranilic acid according to the procedure described in Example 33 (a).

Calcd for $C_9H_7IO_3S$: C, 33.55; H, 2.19; I, 39.40; S, 9.95%. Found: C, 33.70; H, 2.23; I, 39.20; S, 10.09%.

(b) 7-iodo-2,3-cyclohexenothiochromone, m.p. 137°, was prepared from S-acetyl-4-iodothiosalicylic acid and 1-(N-pyrrolidino) cyclohexene according to the procedure described in Example 1 (a).

Calcd for $C_{13}H_{11}IOS$: C, 45.64; H, 3.21; I, 37.09; S, 9.37%. Found: C, 45.61; H, 3.44; I, 36.80; S, 9.23%.

(c) 7-cyano-2,3-cyclohexenothiochromone, m.p. 230°–231°, was prepared from 7-iodo-2,3-cyclohexenothiochromone and cuprous cyanide according to the procedure described in Example 1 (b).

The cyano intermediate was converted into the cycloalkenothio chromone (m.p. 290°–293°) according to the procedure described in Example 1 (c).

EXAMPLE 38

7-(5-(1H)-tetrazolyl)-2,3-cyclohexenothiochromone

The cycloalkenothiochromone, m.p. 276°–278° (dec.), was prepared from 7-cyano-2,3-cyclohexenothiochromone and sodium azide according to the procedure described in Example 2.

EXAMPLE 39

7-carboxy-2,3-(4'-ethylcyclohexeno)thiochromone

7-Iodo-2,3-(4'-ethylcyclohexeno)thiochromone m.p. 174°–176°, was prepared from S-acetyl-4-iodothiosalicylic acid and 1-(N-pyrrolidino)-4-ethylcyclohexene according to the procedure described in Example 1 (a).

Calcd for $C_{15}H_{15}IOS$: C, 48.66; H, 4.08; I, 34.28; 58.66%. Found: C, 48.82; H, 4.10; I, 34.12; 58.68%.

7-Cyano-2,3(4'-ethylcyclohexeno)thiochromone, m.p. 204°–205°, was prepared from 7-iodo-2,3-(4'-ethylcyclohexeno) thiochromone and cuprous cyanide according to the procedure described in Example 1 (b).

Calcd for $C_{16}H_{15}NOS$: C, 71.36; H, 5.61; N, 5.20; S, 11.88%. Found: C, 71.16; H, 5.54; N, 4.99; S, 12.06%.

The cyano intermediate was converted into the cycloalkenothiochromone (m.p. 281°–283°) according to the procedure described in Example 1 (c).

Calcd for $C_{16}H_{16}O_3S$: C, 66.64; H, 5.59; S, 11.12%. Found: C, 66.72; H, 5.47; S, 11.24%.

EXAMPLE 40

7-carboxy-2,3-(4'-ethylcyclohexeno)-thiochromone-1,1-dioxide

The cycloalkenothiochromone, m.p. 266°–268°, was prepared by oxidation of 7-carboxy-2,3-(4'-ethylcyclohexeno)thiochromone with hydrogen peroxide in glacial acetic acid according to the procedure described in Example 32.

Calcd for $C_{16}H_{16}O_5S$: C, 59.98; H, 5.03; S, 10.01%. Found: C, 60.18; H, 5.03; S, 9.97%.

EXAMPLE 41

7-(5-(1H)-tetrazolyl-2,3(4'-ethylcyclohexeno)thiochromone

The cycloalkenothiochromone, m.p. 274°–276°, was prepared from 7-cyano-2,3-(4'-ethylcyclohexeno)thiochromone and sodium azide according to the procedure described in Example 2.

Calcd for $C_{16}H_{16}N_4OS$: C, 61.51; H, 5.16; N, 17.94; S, 10.26%. Found: C, 61.91; H, 5.02; N, 17.51; S, 10.10%.

EXAMPLE 42

7-(5-(1H)-tetrazolyl)-2,3-(4'-ethylcyclohexenothiochromone-1,1-dioxide

The cycloalkenothiochromone, m.p. 220°–222°, was prepared by oxidation of 7-(5-(1H)-tetrazolyl-2,3-(4'-ethylcyclohexeno)thiochromone with hydrogen peroxide in glacial acetic acid according to the procedure described in Example 32.

The compounds of the present invention are useful in providing relief of allergic conditions, such as asthma in an individual, for whom such therapy is indicated. For example, the compounds can be used prophylactically, to prevent the onset of allergic symptoms. The anti-allergic effect is produced by administering to that individual a therapeutically effective anti-allergic amount of a compound as presently claimed. The term "individual" as utilized in this specification means a human being or an experimental animal that is a model for a human being. "Therapeutically effective amount" means a dosage or a series of dosages that is effective in producing an inhibition of allergic response in an individual. Medical indications for the use of the anti-allergics of the present invention are any conditions in which it is desired to treat allergy in an individual. Although the required therapeutic amount will vary from individual to individual and from indication to indication, it is easily determined by one skilled in the art without undue experimentation. Dose forms for the administration of the anti-allergic can be prepared by recognized methods in the pharmaceutical sciences. The compounds may be administered by inhalation, injection or other suitable routes of administration.

For the treatment of asthma, the composition may be in a form suitable for administration by inhalation. Thus the compositions may comprise a suspension or solution of the active ingredient in water or in a suitable alcohol for administration as an aerosol by means of a conventional nebulizer. Alternatively, the compositions may comprise a suspension or solution of the active ingredient in a conventional liquified propellant to be administered as an aerosol from a pressurized container. The compositions may also comprise the solid active ingredient in a solid diluent for administration from a powder inhalation device. Other routes of administration, e.g. sublingual, oral or buccal tablets, rectal suppositories or intravenous injection or infusion may also be used.

The compositions may also contain, in addition to the compound of general formula I, other active ingredients, for instance, bronchodilators, e.g., those of the β-adrenergic type, such as iso- or orci-prenaline or salbutamol or a pharmaceutically acceptable salt thereof. The compositions may contain 0.1 to 10% by weight of the compound of general formula I. If salbutamol or iso- or orci-prenaline sulphate or used, they are suitably present in a concentration of 0.1 to 5% by weight.

The anti-allergic activity was determined by measuring the inhibition of allergic release of spasmogens from mast cells, using the method of Taylor et al., as described in Int. Arch. Allergy, 46, 104(1974).

The inhibition of spasmogen release from mast cells involved obtaining pools of mast cells from normal rats. For each experiment involving pools of mast cells, 10 or more rats were killed by decapitation. The peritoneal fluid from the animals was pooled and the pool dispensed into small polyethylene tubes (100 μ/tube) containing 25 μl of a degranulating agent phospholipase A (PL-A), and 25 μl of the drug to be tested. Each treatment was repeated in at least four tubes. All the tubes were incubated at 37° C. for ten minutes. The mast cells were fixed and and stained by addition of 50 μl/tube of 2.5% toluidine blue made up in 25% acetic acid. The proportion of mast cells undergoing degranulation was assessed by counting under the microscope. At least 25 mast cells were counted from each tube. The percentage inhibition of degranulation resulting from each treatment was calculated using the formula $100[1-(x-z)/(y-z)]$, where 'x' represents the mean percentage of cells undergoing degranulation in the tubes treated with PL-A and drug, 'y' represents the mean percentage of cells undergoing degranulation in the tubes treated with PL-A only, and "z" represents the mean percentage of cells undergoing degranulation in the PL-A-negative tubes.

The compounds were tested against disodium cromogylcate, which has been shown to be an effective inhibitor of experimental allergen-induced bronchoconstriction in asthmatics. The cromoglycate compound has also been shown to specifically inhibit the allergic release of spasmogens in immediate hypersensitivity reactions in several animals. [See Nature, Vo. 223, 197 (1969)].

The inhibitory concentrations of compounds of formula I, expressed in millimols required to inhibit the degranulation of mast cells by 20%, ($I.C._{20}$ values), together with the relative potency of the tested compounds in relation to disodium cromogylcate, are given below.

The test results indicate that all of the compounds listed above are effective in inhibiting the allergic release of spasmogens and are therefore useful in the management of allergic reactions, such as bronchial asthma.

| | INHIBITION OF MAST CELL DEGRANULATION BY CYCLOALKENO(THIO)CHROMONES | | |
|---|---|---|---|
| Example No. | Compound Name | $IC_{20}$ (μ moles) | Relative Potency |
| 1 | 6-Carboxy-2,3-cyclohexenochromone | 2.1 | 3.1 |
| 2 | 6-(5-(1H)-tetrazolyl)-2,3-cyclohexenochromone | 1.7 | 3.8 |
| 3 | 6-Carboxy-2,3-(4'-methylcyclohexeno)chromone | 6.5 | 1.0 |
| 4 | 6-(5-(1H)-tetrazolyl)-2,3-(4'-methylcyclohexeno)chromone | 4.5 | 1.4 |
| 5 | Sodium-6-carboxy-2,3-(4'-ethylcyclohexeno)chromone | 0.58 | 11.2 |
| 6 | Sodium-6-(5-(1H)-tetrazolyl)-2,3-(4'-ethylcyclohexeno)chromone | 1.0 | 6.5 |
| 7 | 6-Carboxy-2,3-(4'-carboxycyclohexeno)chromone | 6.5 | 1.0 |
| 8 | 6-(5-(1H)-tetrazolyl)-2,3-(4'-ethoxycarbonylcyclohexeno)chromone | 4.2 | 1.6 |
| 13 | 6-(5-(1H)-tetrazolyl)-2,3-cyclooctenochromone | 1.3 | 5.0 |
| 15 | 6-carboxy-2,3-(4'-benzyloxycyclohexeno)chromone | 4.3 | 1.5 |
| 18 | 6-Methylthio-2,3-(4'-carboxycyclohexeno)chromone | 1.3 | 5.0 |
| 20 | 6-Methylsulfonyl-2,3-(4'-carboxycyclohexeno)chromone | 1.9 | 3.4 |
| 21 | 6-Carboxy-2,3-(4'-methoxycyclohexeno)chromone | 1.8 | 3.6 |
| 24 | 7-Carboxy-2,3-cyclohexenochromone | 2.1 | 3.1 |
| 25 | 7-(5-(1H)-tetrazolyl)-2,3-cyclohexenochromone | 0.9 | 7.2 |
| 26 | 7-Carboxy-2,3-(4'-ethylcyclohexeno)chromone | <0.6 | >13.0 |
| 27 | 7-(5-(1H)-tetrazolyl)-2,3-(4'-ethylcyclohexeno)chromone | <0.6 | >13.0 |
| 31 | 6-(5-(1H)-tetrazolyl)-2,3-(4'-methyl-4'-phenylcyclohexeno)- | 1.5 | 4.3 |
| 32 | 6-Carboxy-2,3-(4'-ethylcyclohexeno)thiochromone-1,1-dioxide | 0.6 | 10.8 |
| 33 | 6-Carboxy-2,3-(4'-ethylcyclohexeno)thiochromone | 4.6 | 1.41 |
| 35 | 6-(5-(1H)-tetrazolyl)-2,3-(4'-ethylcyclohexeno)thiochromone | 0.36 | 18.1 |

What is claimed is:

1. A compound of the formula,

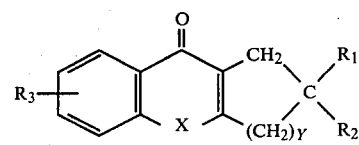

and pharmacologically acceptable non-toxic salts thereof wherein:

X is selected from the group consisting of —O—, —S— and —$SO_2$—;

Y is 1 to 4;

$R_1$ is hydrogen or alkyl having from 1 to 3 carbon atoms;

$R_2$ is selected from the group consisting of hydrogen, alkyl having from 1 to 3 carbon atoms, phenyl, carboxyl, alkoxy having from 1 to 2 carbon atoms, benzyloxy, and alkoxy-carbonyl having from 2 to 3 carbon atoms, with the proviso that when R₁ is alkyl, R₂ is hydrogen, alkyl or phenyl;

R₃ is selected from the group consisting of carboxyl, methylthio, methylsulfonyl, methylsulfinyl, alkoxycarbonyl having from 2 to 3 carbon atoms, and tetrazolyl, with the proviso that at least one of R₂ and R₃ is alkoxycarbonyl, carboxyl or tetrazolyl.

2. A compound as claimed in claim 1 in which Y is 2, R₁ is hydrogen, R₂ is ethyl, and R₃ is tetrazolyl, or, R₂ is carboxyl and R₃ is methylthio, methylsulfonyl or methylsulfinyl, wherein R₃ is in the 6- or 7-position, and its sodium salt.

3. A compound as claimed in claim 2 wherein R₂ is carboxyl, and R₃ is methylthio.

4. A compound as claimed in claim 1 which is 6-carboxy-2,3-cyclohexenochromone or its sodium salt.

5. A compound as claimed in claim 1 which is 6-(5-(1H)-tetrazolyl)-2,3-cyclohexenochromone or its sodium salt.

6. A compound as claimed in claim 1 which is 6-carboxy-2,3-(4'-methylcyclohexeno)chromone or its sodium salt.

7. A compound as claimed in claim 1 which is 6-(5-(1H)-tetrazolyl)-2,3-(4'-methylcyclohexeno)chromone or its sodium salt.

8. A compound as claimed in claim 1 which is sodium-6-carboxy-2,3-(4'-ethylcyclohexeno)chromone or its sodium salt.

9. A compound as claimed in claim 1 which is sodium-6-(5-(1H)-tetrazolyl)-2,3-(4'-ethylcyclohexeno)chromone or its sodium salt.

10. A compound as claimed in claim 1 which is 6-carboxy-2,3-(4'-carboxycyclohexeno)chromone or its sodium salt.

11. A compound as claimed in claim 1 which is 6-(5-(1H)-tetrazolyl)-2,3-(4'-ethoxycarbonylcyclohexeno)chromone or its sodium salt.

12. A compound as claimed in claim 1 which is 6-(5-(1H)-tetrazolyl)-2,3-cyclooctenochromone or its sodium salt.

13. A compound as claimed in claim 1 which is 6-carboxy-2,3-(4'-benzyloxycyclohexeno)chromone or its sodium salt.

14. A compound as claimed in claim 1 which is 6-methylthio-2,3-(4'-carboxycyclohexeno)chromone or its sodium salt.

15. A compound as claimed in claim 1 which is 6-methylsulfonyl-2,3-(4'-carboxycyclohexeno)chromone or its sodium salt.

16. A compound as claimed in claim 1 which is 6-carboxy-2,3-(4'-methoxycyclohexeno)chromone or its sodium salt.

17. A compound as claimed in claim 1 which is 7-carboxy-2,3-cyclohexenochromone or its sodium salt.

18. A compound as claimed in claim 1 which is 7-(5-(1H)-tetrazolyl)-2,3-cyclohexenochromone or its sodium salt.

19. A compound as claimed in claim 1 which is 7-carboxy-2,3-(4'-ethylcyclohexeno)chromone or its sodium salt.

20. A compound as claimed in claim 1 which is 7-(5-(1H)-tetrazolyl)-2,3-(4'-ethylcyclohexeno)chromone or its sodium salt.

21. A compound as claimed in claim 1 which is 6-carboxy-2,3-(4'-ethylcyclohexeno)thiochromone or its sodium salt.

22. A compound as claimed in claim 1 which is 6-carboxy-2,3-(4'-ethylcyclohexeno)thiochromone-1,1-dioxide or its sodium salt.

23. A compound as claimed in claim 1 which is 6-(5-(1H)-tetrazolyl)-2,3-(4'-methyl-4'-phenylcyclohexeno)-chromone or its sodium salt.

24. A compound as claimed in claim 1 which is 6-(5-(1H)-tetrazolyl)-2,3-(4'-ethylcyclohexeno)-thiochromone or its sodium salt.

25. A therapeutic method for producing an anti-allergic effect in an individual for whom such therapy is indicated, comprising: administering to the individual an effective antiallergic amount of a compound of the formula,

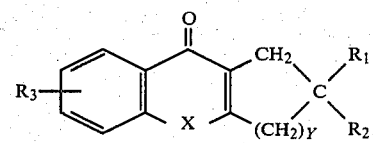

and pharmacologically acceptable non-toxic salts thereof wherein:

X is selected from the group consisting of —O—, —S— and —SO₂—;

Y is 1 to 4;

R₁ is hydrogen or alkyl having from 1 to 3 carbon atoms;

R₂ is selected from the group consisting of hydrogen, alkyl having from 1 to 3 carbon atoms, phenyl, carboxyl, alkoxy having from 1 to 2 carbon atoms, benzyloxy, and alkoxycarbonyl having from 2 to 3 carbon atoms, with the proviso that when R₁ is alkyl, R₂ is hydrogen, alkyl or phenyl;

R₃ is selected from the group consisting of carboxyl, methylthio, methylsulfonyl, methylsulfinyl, alkoxycarbonyl having from 2 to 3 carbon atoms, and tetrazolyl, with the proviso that at least one of R₂ and R₃ is alkoxycarbonyl, carboxyl or tetrazolyl.

26. A therapeutic method as claimed in claim 25, wherein the compound is administered to produce an antiallergic effect in an individual having asthma.

27. A therapeutic method as claimed in claim 25 wherein the compound administered has the formula:

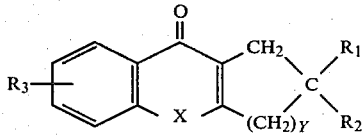

wherein:

Y is 2;

R₁ is hydrogen;

R₂ is ethyl, and R₃ is carboxyl or tetrazolyl; or

R₂ is carboxyl and R₃ is methylthio, methylsulfinyl or methylsulfonyl, wherein R₃ is in the 6- or 7-position, and its sodium salt.

28. A therapeutic method as claimed in claim 26 wherein the compound is administered by inhalation.

29. A compound of the formula,

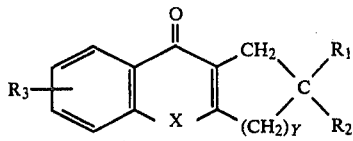

wherein:
X is —O—;
Y is 1 to 4;
R₁ is hydrogen or alkyl having from one to three carbon atoms;
R₂ is selected from the group consisting of hydrogen, alkyl having from 1 to 3 carbon atoms, phenyl, carboxyl, alkoxy having from 1 to 2 carbon atoms, benzyloxy, and alkoxycarbonyl having from 2 to 3 carbon atoms, with the proviso that when R₁ is alkyl, R₂ is hydrogen, alkyl or phenyl; and
R₃ is tetrazolyl.

30. A compound as claimed in claim 29 in which Y is 2; and R₁ is hydrogen.

31. A compound as claimed in claim 29 which is 6-(5-(1H)-tetrazolyl)-2,3-(4′-isopropylcyclohexeno)-chromone.

32. A compound as claimed in claim 29 which is 6-(5-(1H)-tetrazolyl)-2,3-(4′-benzyloxycyclohexeno)-chromone.

33. A compound as claimed in claim 29 which is 7-(5-(1H)-tetrazolyl)-2,3-cyclopentenochromone.

34. A compound as claimed in claim 29 which is 6-(5-(1H)-tetrazolyl)-2,3-(4′,4′-dimethylcyclohexeno)-chromone.

35. A therapeutic method for producing an antiallergic effect in an individual for whom such therapy is indicated, comprising: administering to the individual an effective antiallergic amount of a compound of the formula,

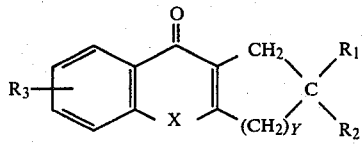

wherein:
X is —O—;
Y is 1 to 4;
R₁ is hydrogen or alkyl having from 1 to 3 carbon atoms;
R₂ is selected from the group consisting of hydrogen, alkyl having from 1 to 3 carbon atoms, phenyl, carboxyl, alkoxy having from 1 to 2 carbon atoms, benzyloxy, and alkoxycarbonyl having from 2 to 3 carbon atoms, with the proviso that when R₁ is alkyl, R₂ is hydrogen, alkyl or phenyl; and
R₃ is tetrazolyl.

36. A therapeutic method as claimed in claim 35 wherein the compound is administered to produce an antiallergic effect in an individual having asthma.

* * * * *